(12) United States Patent
Chin et al.

(10) Patent No.: US 10,278,993 B2
(45) Date of Patent: May 7, 2019

(54) CELL-BASED COMPOSITION AND USE THEREOF FOR TREATMENT OF ACUTE STROKE

(71) Applicant: Cytopeutics Sdn. Bhd., Selangor (MY)

(72) Inventors: Bernard Sze-Piaw Chin, Selangor (MY); Kong Yong Then, Selangor (MY); Soon Keng Cheong, Selangor (MY)

(73) Assignee: Cytopeutics Sdn. Bhd., Selangor (MY)

( * ) Notice: Subject to any disclaimer, the term of this patent is extended or adjusted under 35 U.S.C. 154(b) by 13 days.

(21) Appl. No.: 15/597,724

(22) Filed: May 17, 2017

(65) Prior Publication Data

US 2017/0340675 A1 Nov. 30, 2017

(30) Foreign Application Priority Data

May 25, 2016 (MY) .......................... PI 2016701898

(51) Int. Cl.
*A61K 35/28* (2015.01)
*A61K 9/00* (2006.01)

(52) U.S. Cl.
CPC ............ *A61K 35/28* (2013.01); *A61K 9/0019* (2013.01)

(58) Field of Classification Search
None
See application file for complete search history.

(56) References Cited

U.S. PATENT DOCUMENTS

2007/0269887 A1* 11/2007 Coelho ............... A61M 1/0209
435/366
2012/0201791 A1* 8/2012 Yoo ........................ A61K 35/28
424/93.7

OTHER PUBLICATIONS

McDonald, Courtney A; et al; "Evaluation of the safety and tolerability of a high-dose intravenous infusion of allogeneic mesenchymal precursor cells" Cytotherapy, 17, 1178-1187, 2015 (Year: 2015).*
Kurozumi et al "BDNF Gene-Modified Mesenchymal Stem Cells Promote Functional Recovery and Reduce Infarct Size in the Rat Middle Cerebral Artery Occlusion Model" Molecular Therapy vol. 9, pp. 189-197, 2004.

* cited by examiner

*Primary Examiner* — David W Berke-Schlessel
(74) *Attorney, Agent, or Firm* — Cesari and McKenna, LLP

(57) ABSTRACT

A method for the treatment of acute stroke in a subject by administering to said subject an effective amount of a cell-based composition containing a suspension of mesenchymal stem cells in crystalloid with a cellular concentration from 0.01 million to 3.0 million cells/ml.

16 Claims, 4 Drawing Sheets

Adipogenesis

Chondrogenesis

Osteogenesis

CELL-BASED COMPOSITION AND USE THEREOF FOR TREATMENT OF ACUTE STROKE

CROSS-REFERENCE TO RELATED APPLICATIONS

The present application claims the benefit of Malaysian Application No. PI 2016701898, filed on May 25, 2016, which is hereby incorporated by reference.

FIELD OF THE INVENTION

The present invention relates to a cell-based composition and use thereof for treatment of acute stroke.

BACKGROUND OF THE INVENTION

Stroke is a debilitating condition described as loss of cerebral function, with symptoms lasting 24 hours or longer or leading to death. Stroke involving the middle cerebral arteries confers significant mortality and morbidity due to irreversible neuronal damage. In 2015, World Health Organization (WHO) reported that stroke has claimed 6.7 million deaths globally and is one of the main cause of disability in adults.

Various treatment methods have been developed in the past for treatment of acute stroke. Conventionally, one of the common ways of managing acute stroke is carried out by means of thrombolytic therapy. However, studies seem to suggest that thrombolytic therapy had not garnered much success on significantly improving overall health for patients afflicted by acute stroke.

In light of the above, alternative ways for treating acute stroke which are safer, non-invasive and clinically effective became focus of investigation for medical experts. Studies on mesenchymal stem cells, also known as mesenchymal stromal cells, have generated a lot of interest among researchers and clinicians due to its attributes which include ability of differentiating into neuron-like cells and immunomodulatory properties. Mesenchymal stem cells may also help attenuate cerebral oedema and hasten recovery following acute stroke. Furthermore, blood-brain barrier is semi-permeable in the acute stroke period which allows mesenchymal stem cells to be administered intravenously. Kurozumi et al. reported that mesenchymal stem cells transplantation is able to ameliorate stroke in rat models.

However, studies and research publications on treating acute stroke using cell-based methods in humans appears to be lacking. Accordingly, there remains a need for a novel cell-based composition which is clinically safe and therapeutically effective for the treatment of acute stroke in humans.

SUMMARY OF THE INVENTION

In alleviating limitations resulting from conventional methods in the past, the present invention provides a cell-based preparation and use thereof which is clinically safe and therapeutically effective for acute stroke.

More particularly, the present invention relates to a cell-based composition comprising a suspension of mesenchymal stem cells in crystalloid with a cellular concentration from 0.01 million to 3.0 million cells/ml wherein the cell-based composition is used in a form of medicament for treatment of acute stroke.

Thus, one aspect of this invention is a method of treating acute stroke in a subject by administering to the subject (e.g., by intravenous infusion carried out for 0.5 to 2 hours) the cell-based composition described above and hereinafter in a therapeutically effective amount (e.g., 0.25 million to 3.0 million cells/kg body weight).

BRIEF DESCRIPTION OF DRAWINGS

The drawings constitute part of this specification and include an exemplary or preferred embodiment of the invention, which may be embodied in various forms. It should be understood, however, that the disclosed preferred embodiments are merely exemplary of the invention. Therefore the figures disclosed herein are not to be interpreted as limiting, but merely as the basis for teaching one skilled in the art of the invention.

In the appended drawings.

DETAILED DESCRIPTION OF THE INVENTION

Figure 1:
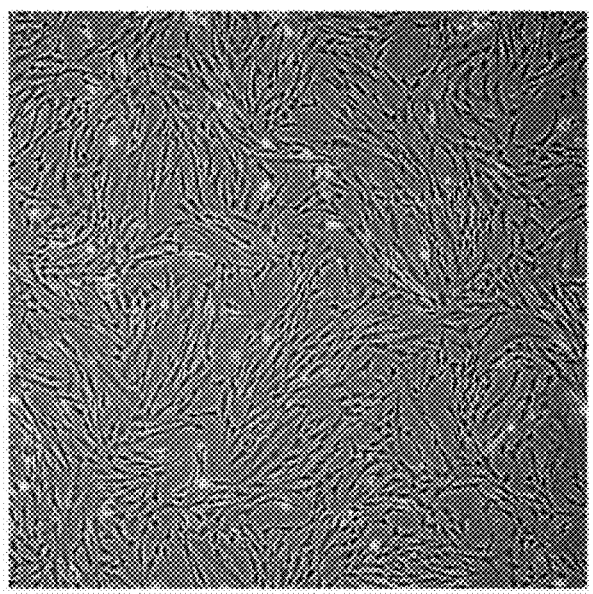
FIG. 1 illustrates morphology of human umbilical cord-derived mesenchymal stem cells.

A detailed description of the present invention is described herein. The present invention is directed to a cell-based composition and use thereof for treating acute stroke. More particularly, the present invention relates to a cell-based composition comprising a suspension of mesenchymal stem cells in crystalloid with a cellular concentration from 0.01 million to 3.0 million cells/ml wherein the cell-based composition is used in a form of medicament for treatment of acute stroke.

In a preferred embodiment of the present invention, accordingly, the mesenchymal stem cells used for preparation of the suspension are derived from various sources including, but not limiting to, human umbilical cord, bone marrow, fat tissue, peripheral blood or tooth pulp. Samples are either collected from mothers post-birth or from healthy donors. If required, the samples are cleaned and disinfected accordingly.

Upon collection, the samples are sent to laboratory to be processed further. The samples will be digested using a digestion enzyme, preferably, but not limiting to collagenase type II and followed by centrifugation, leaving a layer of supernatant and pellet containing mesenchymal stem cells. The mesenchymal stem cells are isolated and cultured in a specially formulated medium supplemented with a combination of various antibiotics and animal-free serum. The cultures are maintained at a temperature range from 35° C. to 40° C., preferably at 37° C. in a humidified atmosphere for 3-4 days.

As it will be apparent to a person of ordinary skill in the art, mesenchymal stem cells are adherent to plastic. Non-adherent cells are discarded and the growth medium is replaced every 3-4 days until the cells reached confluence.

Upon reaching 70%-80% confluence, the adherent mesenchymal stem cells are incubated with a dissociation enzyme, preferably, but not limiting to trypsin and re-plated at $1\times10^4$ cells/ml for a series of passages, preferably, but not limiting to 3-4 passages. The mesenchymal stem cells are then harvested in a culture flasks, thus expanding population of the cells.

The mesenchymal stem cells are characterized in accordance to a criteria set forth by International Society for Cellular Therapy (ISCT). Apart from adherence to plastic, established criteria defining mesenchymal stem cells include expression of antigen markers as measured by flow cytometry and tri-differentiation ability of the cells (Dominici 2006). Using flow cytometry, the mesenchymal stem cells are defined by expression of CD73, CD90, and CD105 markers whilst absence of expression for CD34, CD45, and HLA-DR markers. Meanwhile, the tri-differentiation ability of the mesenchymal stem cells is demonstrated by way of the cells differentiating into osteoblasts, adipocytes and chondroblasts.

Once the population of mesenchymal stem cells have been expanded, a disassociation enzyme, preferably, but not limiting to trypsin is added in to the flasks and incubated at a temperature range from 35° C. to 40° C., more preferably at 37° C., for a period of 1-15 minutes, more preferably for 5 minutes to detach the plastic-adherent mesenchymal stem cells, leaving the cells slightly shrunk. Next, the flasks are gently tapped to dislodge the cells and medium is further added to dilute the trypsin, forming a mesenchymal cell suspension. The cell suspension is then transferred into 50 ml centrifuge tubes and centrifuged at a speed range from 300 g to 800 g, more preferably at 500 g at a temperature range from 18° C. to 20° C. for 10 minutes forming a layer of supernatant with pellet at bottom of the tubes. The supernatant is removed, leaving the pellet of mesenchymal stem cells in the tubes.

The pellet of mesenchymal stem cells are re-suspended in a sterile cryovial of 1.8 ml in size containing cryopreservation medium comprising from 80% to 90% animal-free serum and a cryoprotectant, preferably, but not limiting to dimethyl sulfoxide from 1% to 10%. Alternatively, dimethyl sulfoxide may also be substituted with human serum albumin. Typically, a cryovial contains from 25 million to 30 million cells per vial. Alternatively, cryovials of up to 5 ml in size may also be used.

The mesenchymal stem cells in cryovials are frozen in a controlled rate freezer until −70 to −90° C. but preferably −90 gradually before transferring into quarantine tank, preferably, but not limiting to a vapour phase liquid nitrogen storage tank.

To prepare a cell-based composition for the treatment of acute stroke, the cryopreserved mesenchymal stem cells in cryovials are first thawed at a temperature ranging from 30° C. to 40° C., preferably at 37° C. in a water bath or an incubator for a period from 1 to 5 minutes, more preferably at 2 minutes. Next, the cells are then transferred into new sterile cryovials and are washed with sterile saline, preferably but not limiting to 0.9% sodium chloride. The washed cells in the sterile cryovials will then be centrifuged at a speed ranging from 500×g to 1000×g, preferably at 800×g for a period from 3 to 10 minutes, more preferably for 5 minutes at room temperature, forming a layer of supernatant and a pellet of mesenchymal stem cells.

Typically, the supernatant is removed and discarded, leaving the pellet of mesenchymal stem cells in the cryovial. In one preferred embodiment of the present invention, the pellet of mesenchymal stem cells are then re-suspended with sterile saline at a volume ranging from 5 to 20 ml, preferably at 10 ml, forming a suspension of mesenchymal stem cells.

In another preferred embodiment of the present invention, a cell-based composition is prepared by infusing the suspension of mesenchymal stem cells into crystalloid to reach a cellular concentration from 0.01 million to 3.0 million cells/ml. The crystalloid includes, but not limiting to normal or half-normal saline or colloid.

Exact amount of cells per kg body weight to be administered into a patient depends on variety of factors including body weight, route of administration, age and gender of the patient, and also the type of mechanism of action targeted. Typically, the therapeutically effective amount of the cell-based composition used for the treatment of acute stroke is from to 0.25 million to 3.0 million cells/kg body weight.

The following examples further illustrate but by no means limit the scope of the invention:

Example 1: Collection and Handling of Umbilical Cord Sample

The umbilical cord sample was detached from placenta of a donor post-birth using medical scissors and was immediately submerged in povidone iodine solution for 1-5 minutes to eliminate bacteria and to avoid any risk of contamination. Alternatively, the umbilical may be disinfected using alcohol swab. Upon disinfection, the umbilical cord was then placed in a sterile container of sterile saline solution to maintain moisture. Subsequently, the sterile container was placed into a collection kit and was transported to laboratory using a thermo-insulated bag and kept under a temperature range from 4° C. to 37° C.

The sample was then processed within 48 hours from time of collection.

Example 2: Isolation and Culture of Mesenchymal Stem Cells

First, veins and arteries of the umbilical cord were removed and followed by mincing into 1-2 mm fragments. The fragments were digested with an enzyme, preferably, but not limiting to 0.01% to 0.05% collagenase type II, for a period from 1 to 3 hours, forming a mixture. Next, a centrifugation was carried out to separate the mesenchymal stem cells from the mixture. The mesenchymal stem cells were isolated and then cultured in a growth medium, preferably, but not limiting to Dulbecco's Modified Eagle's Medium (DMEM) which may or may not contain low glucose supplemented with 5-20% animal-free serum and a combination of antibiotics comprising 100 U/mL penicillin, 100 mg/mL streptomycin, 250 ng/mL amphotericin B and 2 mM glutamine. The cultures were maintained at 37° C. in a humidified atmosphere of 5% $CO_2$ and 95% air for 3 days. Non-adherent cells were discarded and the growth medium was replaced every 3-4 days until the cells reached confluence.

Next, the plastic-adherent mesenchymal stem cells were incubated with trypsin and re-plated at $1\times10^4$ cells/ml for 3-4 passages. The mesenchymal stem cells were then harvested in a culture flasks, thus expanding population of the cells.

FIG. 1 illustrates the morphology of the mesenchymal stein cells.

Example 3: Characterization of Mesenchymal Stem Cells

Immunophenotyping

Figure 2:
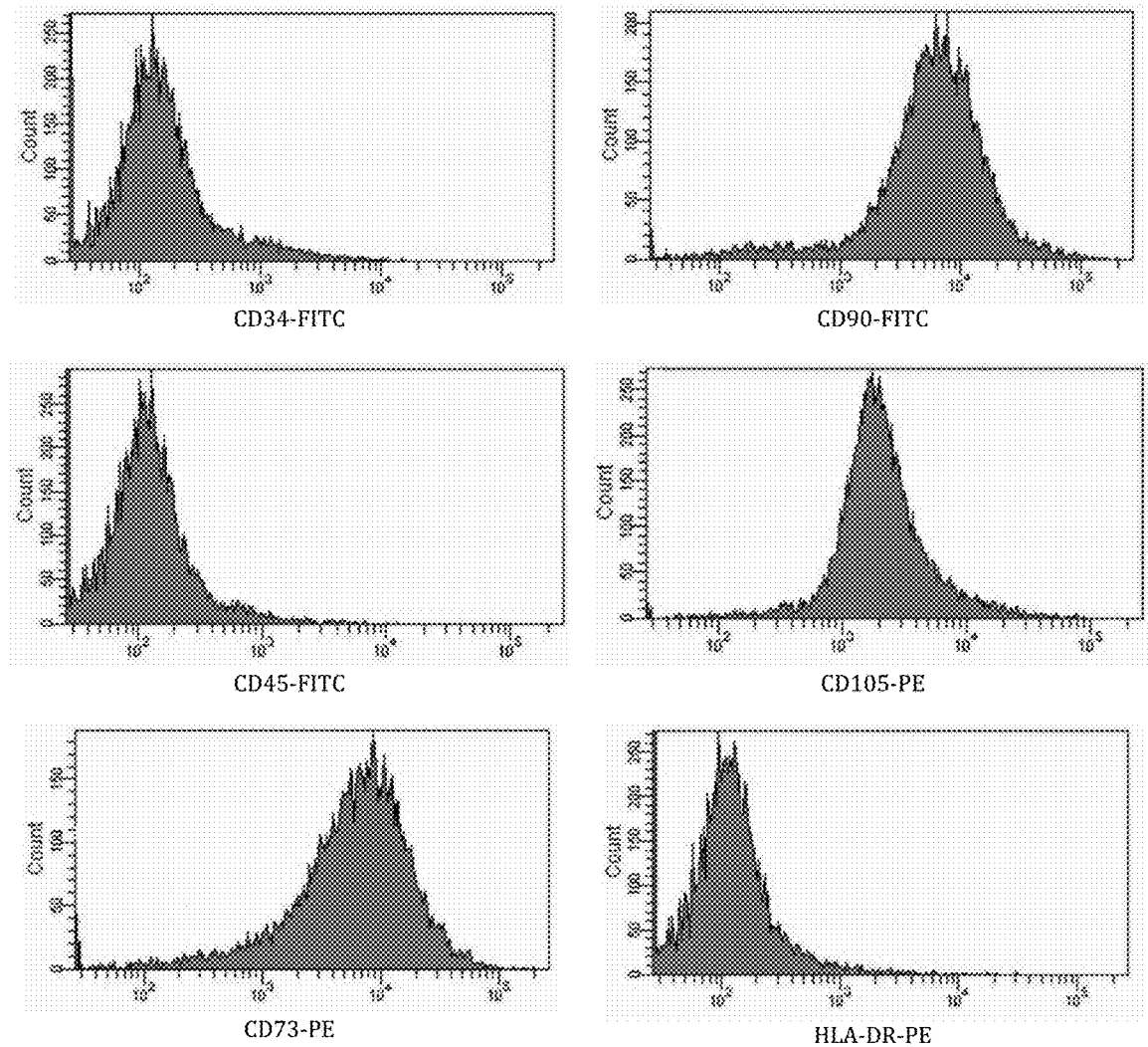
FIG. 2 illustrates immunophenotyping assay results of the mesenchymal stem cells.

The mesenchymal stem cells were immunophenotyped at passage three using isotype (fluorescein isothiocyanate) FITC and (phycoerythrin) PE controls with antigen markers which include CD34, CD45, CD73, CD90, CD105 and HLA-DR. As shown in FIG. 2, the immunophenotyping assay results for the mesenchymal stem cells validate expression for CD73, CD90 and CD105 whilst lacking expression for CD34, CD45 and HLA-DR.

Differentiation Assay

To perform this assay, a selection of specially formulated differentiation medium were used to induce tri-differentiation ability of the mesenchymal stem cells.

Adipogenesis: The mesenchymal stem cells were treated in adipogenic differentiation medium comprising complete medium supplemented with 1 mM dexamethasone and 0.2 mM indomethacin, 0.01 mg/mL insulin and 0.5 mM 3-isobutil-1-metil-xantina. The medium was replaced every 3 days, and the differentiated cells were subjected to Oil Red O staining after about 14 days of culture.

Chondrogenesis: The mesenchymal stem cells were cultured in pellet form and maintained in a chemically defined basal medium comprising complete medium supplemented with 50 mg/mL ascorbate-2-phosphate, 1.0 mM sodium piruvate, 40 mg/mL proline, 10 ng/mL transforming growth factor-b3, 6.25 mg/mL human insulin, 6.25 mg/mL transferrin, 6.25 mg/mL bovine insulin, 6.25 mg/mL selenous acid, 1.25 mg/mL linoleic acid, and 5.35 mg/mL bovine serum albumin. Next, the cells were suspended in 1 mL of chondrogenic medium and replaced every 3-4 days. Chondrogenic pellets were harvested after 5 weeks in culture. To assess chondrogenesis, Alcian Blue was used to stain cartilage matrix.

Osteogenesis: The mesenchymal stem cells were treated in osteogenic differentiation medium comprising complete medium supplemented with 50 mg/mL ascorbate-2-phosphate, 10 mM b-glycerophosphate, and 100 nM dexamethasone. The medium was replaced every 3 days continuously for 2-3 weeks. Alizarin Red S was used to stain matrix mineralization associated with differentiated osteocytes.

Figure 3:
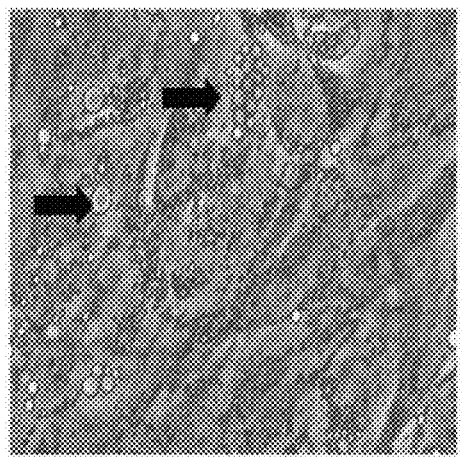
FIG. 3 illustrates adipogenesis, osteogenesis and chondrogenesis of the mesenchymal stem cells respectively.
Figure 3:
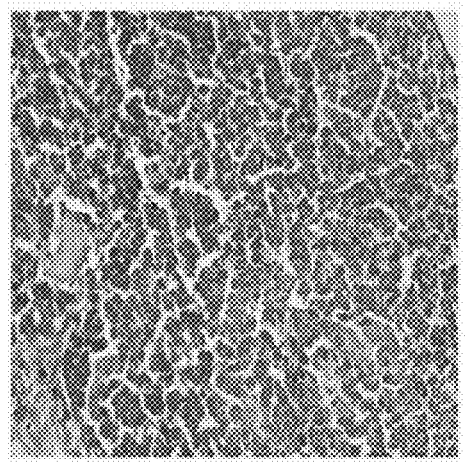
Figure 3:
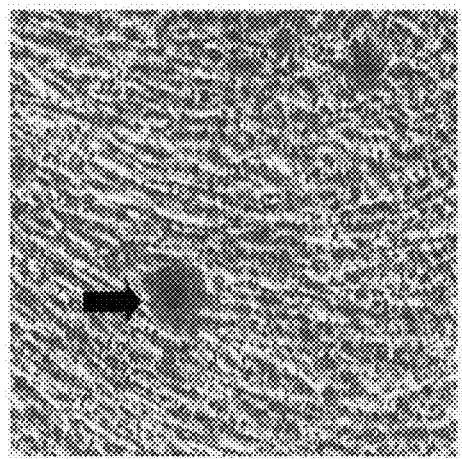

FIG. 3 demonstrates the tri-differentiation ability of the mesenchymal stem cells exhibiting adipogenesis, osteogenesis and chondrogenesis respectively.

Example 4: Cryopreservation of Mesenchymal Stem Cells

Once the population of mesenchymal stem cells was expanded, trypsin was added in to the flasks and incubated at 37° C., for 5 minutes to detach the plastic-adherent mesenchymal stem cells, leaving the cells slightly shrunk. Next, the flasks were gently tapped to dislodge the cells and medium was further added to dilute the trypsin, forming a mesenchymal cell suspension. The cell suspension was then transferred into 50 ml centrifuge tubes and centrifuged at 500 g at a temperature ranging from 18° C. to 30° C. for 10 minutes forming a layer of supernatant with pellet at bottom of the tubes. The supernatant was removed, leaving the pellet of mesenchymal stem cells in the tubes.

The pellet of mesenchymal stem cells were re-suspended in a sterile cryovial containing cryopreservation medium comprising up to 90% animal-free serum and up to 10% dimethyl sulfoxide and were cryopreserved in a controlled freezing gradual rate at −90° C. before being transferred into a quarantine tank at −190° C.

Example 5: Preparation of the Cell-Based Composition for Treatment

The cryopreserved mesenchymal stem cells in cryovials were thawed at 37° C. in a water bath or an incubator for 2 minutes. Next, the cells were then transferred into new sterile cryovials and were washed with 0.9% sodium chloride. The washed cells in the sterile cryovials were then centrifuged at 800×g for 3-10 minutes at room temperature, forming a layer of supernatant and a pellet of mesenchymal stem cells. The supernatant was removed using a sterile syringe, leaving the pellet of mesenchymal stem cells in the cryovial.

The pellet of mesenchymal stem cells was then re-suspended with sterile saline at 10 ml, forming a suspension of mesenchymal stem cells. A cell-based composition was then prepared by infusing the suspension of mesenchymal stem cells into saline at a volume of 250 ml, in a sterile bottle.

Example 6: Treatment Procedure Using the Cell-Based Composition 17 patients with acute middle cerebral artery stroke were recruited and randomized to receive best medical care plus the cell-based composition (Group A-MSC; n=9) or best care medical alone (Group B-Control; n=8). The patients were between 30 to 75 years of age and there were no significant comorbidities. Baseline characteristics of the patients are as shown in TABLE 1.

TABLE 1

Clinical characteristics and other comorbidities in stroke patients at Baseline assessments

| Parameter | Group A (MSC) Mean ± SD | Group B (Control) Mean ± SD | p-value[a] |
|---|---|---|---|
| No. of subjects | 9 | 8 | |
| Age | 57 ± 12 | 64 ± 14 | 0.28 |
| DM (n) | 4 | 4 | |
| HPT (n) | 4 | 7 | |
| HLP (n) | 5 | 5 | |
| IHD (n) | 2 | 1 | |
| TIA (n) | 0 | 0 | |
| Creatinine (μmol/L) | 71.2 ± 20.5 | 70.9 ± 20.9 | 0.98 |
| WBC (×10^9L) | 9.8 ± 4.3 | 13.3 ± 4.3 | 0.13 |
| FBS (mmol/L) | 5.7 ± 1.1 | 7.1 ± 2.2 | 0.15 |
| HbA1c (%) | 6.4 ± 1.1 | 6.0 ± 0.1 | 0.46 |
| Albumin (g/L) | 39.3 ± 3.1 | 34.8 ± 1.0 | 0.01* |
| BPs (mmHg) | 127 ± 20 | 136 ± 10 | 0.23 |
| BPd (mmHg) | 72 ± 11 | 80 ± 10 | 0.14 |
| Heart Rate (beats/min) | 71 ± 14 | 79 ± 22 | 0.47 |
| Smoker (n) | 4 | 1 | |
| Non Smoker/Ex-Smoker (n) | 4 | 7 | |

Independent t-test
*Significant values, p < 0.05
Abbreviation: DM = Diabetes Mellitus; HPT = Hypertension; HLP = Hyperlipidemia; IHD = Ischemic Heart Disease; TIA = Transient Ischemic Attack; WBC = White Blood Cell; FBS = Fasting Blood Sugar; HbA1c = Glycated Haemoglobin; BPs = Systolic Blood Pressure; BPd = Diastolic Blood Pressure; NIHSS = National Institutes of Health Stroke Scale (Score <25: very severe, Score 1-5: Mild severity); mRS = Modified Rankin Scale (Score 0: No symptoms, Score 5: severe disability); Barthel Index (Score >85: nearly complete independence, Score <40: Requires constant care).

Abbreviation

DM=Diabetes Mellitus; HPT=Hypertension; HLP=Hyperlipidemia; IHD s=Ischemic Heart Disease;

TIA=Transient Ischemic Attack; WBC=White Blood Cell; FBS=Fasting Blood Sugar; HbA1c=Glycated Haemoglobin; BPs=Systolic Blood Pressure; BPd=Diastolic Blood Pressure; NIHSS=National Institutes of Health Stroke Scale (Score <25: very severe, Score 1-5: Mild severity); mRS=Modified Rankin Scale (Score 0: No symptoms, Score 5: severe disability); Barthel Index (Score >85: nearly complete independence, Score <40: Requires constant care).

Patients in Group A received a dose of the cell-based composition comprising a total number of cells from 100× $10^6$ cells to 200×$10^6$ cells intravenously at one month after acute stroke. The treatment procedure began with infusion of 200 ml saline into the patients for a period from 45 to 60 minutes. Next, the cell-based composition which was prepared earlier (as described in Example 5) was infused into the patients for a period from 30 minutes to 2 hours. The bottle containing the cell-based composition was shaken gently every 5 minutes to ensure that the cells are suspended in saline homogenously. When the infusion is almost complete, 50 ml of sterile saline was infused into the bottle containing the cell-based composition to rinse and flush out any remaining cells.

Internationally-validated scales of Barthel Index (BI), National Institutes of Health Stroke Scale (NIHSS) and Modified Rankin Score (mRS) were used to record the disability and functional progress at baseline (stroke onset), 6 weeks, 3 months, and 12 months of follow-up.

Barthel Index (BI) is an ordinal scale used to measure performance in activities of daily living. NHISS (The National Institutes of Health Stroke Scale) is a tool used by physicians to measure the impairment caused by a stroke. mRs (The modified Rankin Scale) is a tool used for measuring the degree of disability or dependence in the daily activities in stoke patients.

Example 7: Results and Discussion

Statistical analysis were performed using Statistical Package for the Social Sciences (SPSS version 14.0). Data was presented as:
Numerical data (Mean±SD)
Categorical data [frequency (%)]
Independent t-test was applied to evaluate the differences of follow-up assessments between Group A and Group B as shown in TABLE 1 and TABLE 2. One-way ANOVA was applied to examine the differences between baseline and follow-up visits for both groups as shown in TABLE 3. Statistical significant was established at p<0.05.

NHISS, B1 and mRs Score at BASELINE Between MSC and Control Groups

All patients were severely disabled following acute stroke [Baseline (Mean±SD)] based on the mRS (4±1); BI (14±17) and NIHSS (17±6)], with no difference between both arms.

TABLE 2

NIHSS, BI and mRS score at Baseline

| Parameter | Mean ± SD | | |
|---|---|---|---|
| (Baseline) | Group A (MSC) | Group B (Placebo) | p-value[a] |
| NIHSS | 18 ± 6 | 16 ± 7 | 0.62 |
| Barthel Index | 16 ± 15 | 13 ± 19 | 0.67 |
| mRS | 4 ± 1 | 5 ± 1 | 0.64 |

[a]Independent t-test
* Significant values, p < 0.05

Abbreviation: NIHSS = National Institutes of Health Stroke Scale (Score <25: very severe, Score 1-5: Mild severity); mRS = Modified Rankin Scale (Score 0: No symptoms, Score 5: severe disability); Barthel Index (Score >85: nearly complete independence, Score <40: Requires constant care).
NHISS, BI and mRs score at Baseline and 6 week, 3 M, 6 M, 9 M and 12 M in MSC and control groups Abbreviation NIHSS=National Institutes of Health Stroke Scale (Score <25: very severe, Score 1-5: Mild severity); mRS=Modified Rankin Scale (Score 0: No symptoms, Score 5: severe disability); Barthel Index (Score >85: nearly complete independence, Score <40: Requires constant care).

NHISS, B1 and mRs score at Baseline and 6 week, 3M, 6M, 9M and 12M in MSC and control groups Both groups showed improvement in NIHSS, BI and mRS over time but the improvement was significant in Group A only in which the patients received infusion of the cell-based composition.

TABLE 3

Mean NHISS, Barthel index and mRs score at Baseline and 6 weeks, 3 months, 6 months, 9 months and 12 months after infusion of the cell-based composition

| Parameters | Groups | Baseline | 6 weeks | 3 M | 6 M | 9 M | 12 M | p-value[a] |
|---|---|---|---|---|---|---|---|---|
| NHISS | MSC | 18 ± 6 | 9 ± 2 | 8 ± 3 | 5 ± 3 | 5 ± 3 | 3 ± 2 | <0.001[b] |
| | Placebo | 16 ± 7 | 11 ± 8 | 10 ± 10 | 9 ± 11 | 10 ± 13 | 8 ± 13 | 0.74 |
| Barthel Index | MSC | 16 ± 15 | 70 ± 31 | 79 ± 17 | 85 ± 12 | 86 ± 11 | 91 ± 8 | <0.001[c] |
| | Placebo | 13 ± 19 | 26 ± 38 | 48 ± 43 | 55 ± 46 | 57 ± 51 | 67 ± 58 | 0.27 |
| mRs | MSC | 4 ± 1 | 3 ± 1 | 3 ± 1 | 3 ± 1 | 3 ± 1 | 2 ± 1 | 0.01[d] |
| | Placebo | 5 ± 1 | 4 ± 1 | 4 ± 1 | 3 ± 2 | 3 ± 2 | 2 ± 2 | 0.08 |

[a]One-Way ANOVA test
[b]NHISS score between Baseline against 6 weeks, 3 M, 6 M, 9 M and 12 M were significantly different at p < 0.05 by post-hoc test Scheffe's procedures.
[c]Barthel index score between Baseline against 6 weeks, 3 M, 6 M, 9 M and 12 M were significantly different at p < 0.05 by post-hoc test Scheffe's procedures.
[d]mRs score between Baseline against 12 M only were significantly different at p < 0.05 by post-hoc test Scheffe's procedures.

Figure 4:
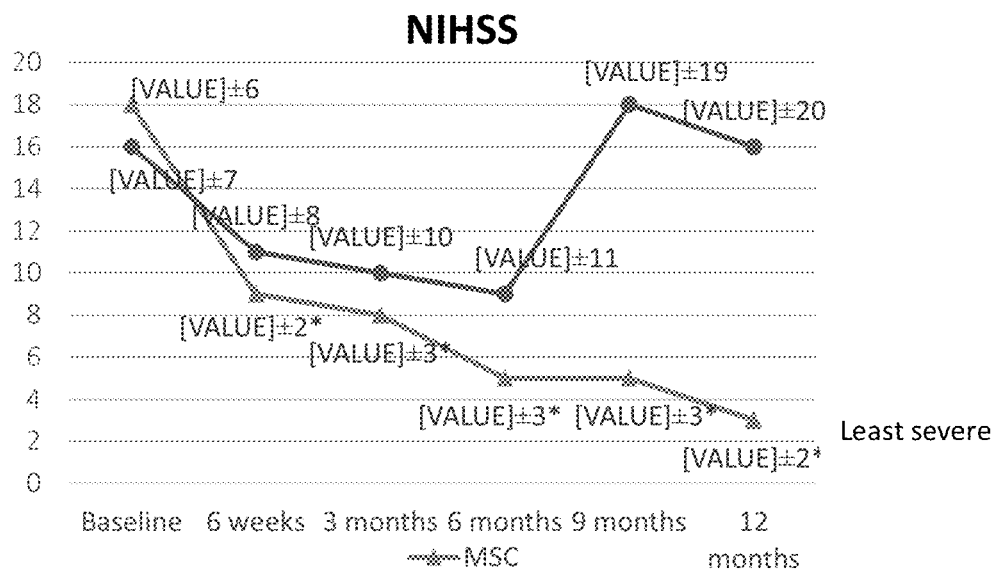
FIG. 4 illustrates mean of National Institutes of Health Stroke Scale (NIHSS) score at baseline and 6 weeks, 3, 6, 9 and 12 months after patients receiving treatment.

FIG. 4 illustrates the mean of NIHSS score at baseline and after 6 weeks, 3, 6, 9 and 12 months of infusion of cell-based composition. As shown in FIG. 4, all patients treated with infusion of cell-based composition presented with severe neurological impairment (defined by NHISS score ≥15) at baseline improved significantly 6 weeks, 3, 6, 9 and 12 months after infusion of cell-based composition with only mild impairment (defined by NHISS score is ≤5). No significant improvement was noticed in control group.

Figure 5:
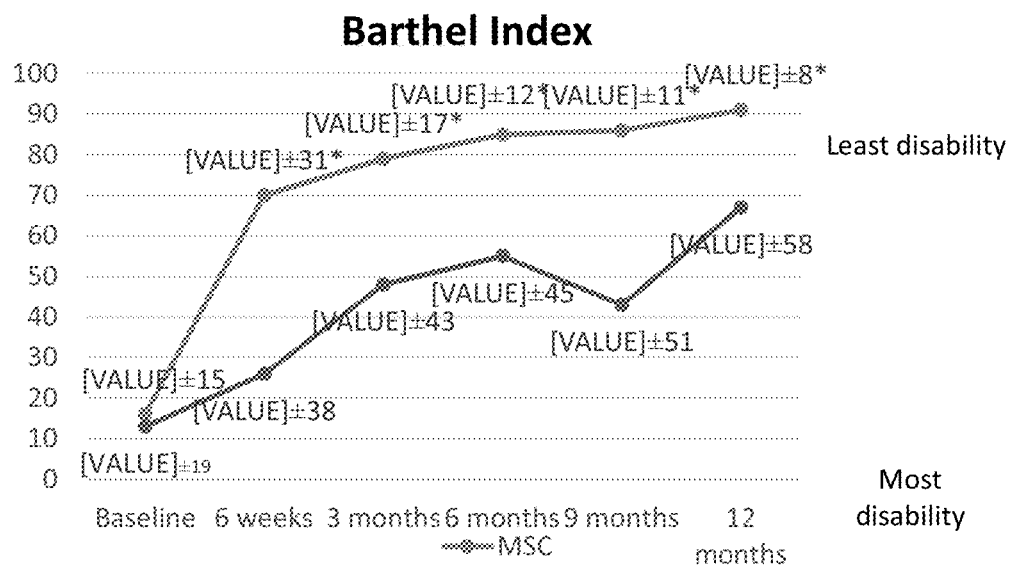
FIG. 5 illustrates mean of Barthel Index (BI) score at baseline and 6 weeks, 3, 6, 9 and 12 months after patients receiving treatment.
Figure 4:
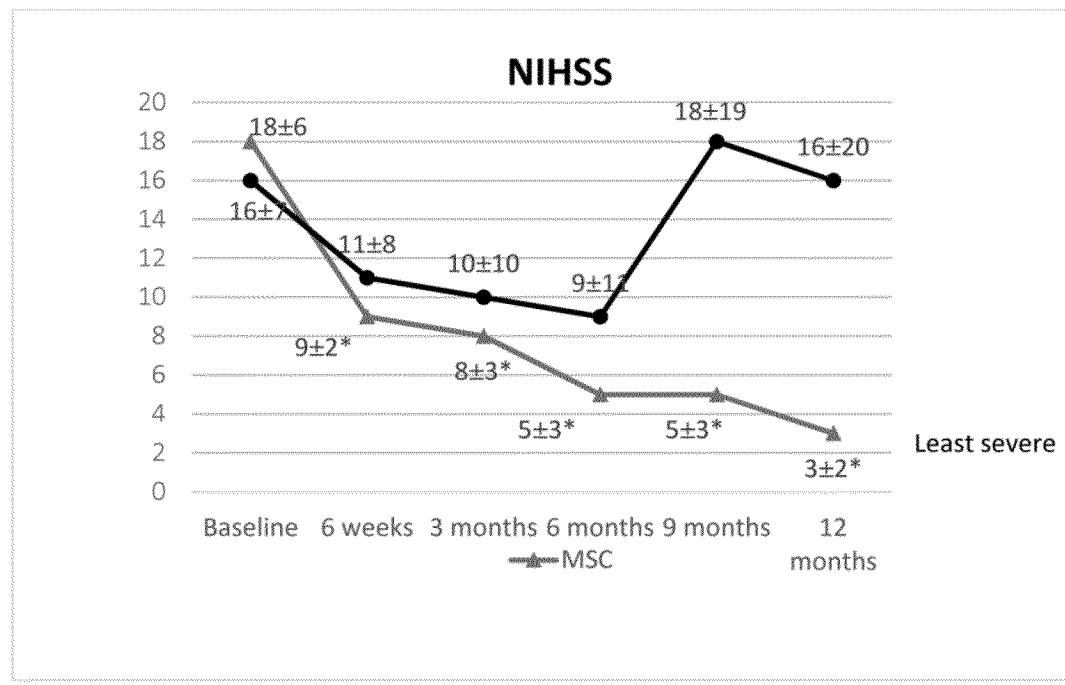
Figure 5:
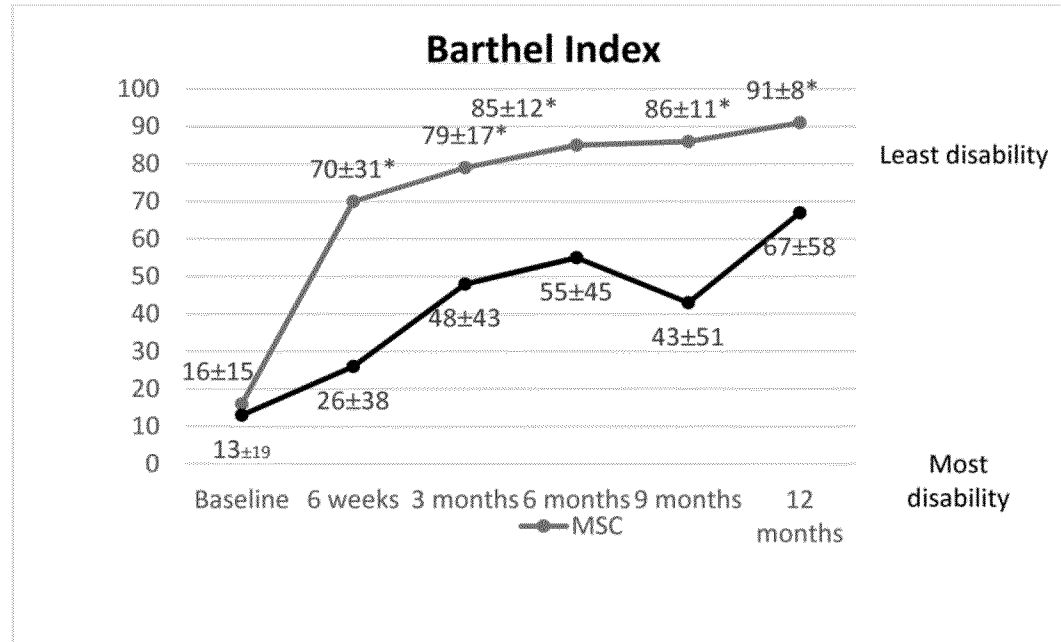

FIG. 5 illustrates the mean of Barthel Index (BI) score at baseline and at 6 weeks, 3, 6, 9 and 12 months after receiving treatment using cell-based composition. As shown in FIG. 5, intergroup comparison revealed that mean BI was higher for Group A at 6-weeks follow-up when compared to Group B (70±31 vs 26±38, p=0.04). As shown in FIG. 5, all patients presented at baseline who needed constant care (defined by BI score <40) improved significantly 6 weeks, 3, 6, 9 and 12 months after infusion of cell-based composition to nearly complete independence (defined by BI score 85-100). No significant improvement was noticed in control group.

Based on the results above, patients who received treatment using cell-based composition benefitted from significant improvement in stroke severity scales and functional recovery as early as 6 weeks of follow up. The benefit was sustained up to 12 months follow-up and may potentially reduce mortality from sepsis. The findings indicate that the cell-based composition administered intravenously in the sub-acute period following severe stroke is safe and efficacious, and results in accelerated recovery in the initial period, reducing the clinical disability and mortality in patients.

Having described preferred embodiments of the present invention with reference to the accompanying drawings, it is not intended that these embodiments and examples illustrate and describe all possible forms of the present invention, and it is to be understood that the present invention is not limited to those precise embodiments, and that various changes and modifications may be effected therein by one skilled in the art without departing from the scope of the invention as defined in the appended claims.

The invention claimed is:

1. A method for the treatment of acute stroke in a subject, said method comprising administering to said subject a therapeutically effective amount of a cell-based composition containing a suspension of mesenchymal stem cells in crystalloid with a cellular concentration from 0.01 million to 3.0 million cells/ml wherein the administering step is performed during the sub-acute period after the subject suffers an acute stroke.

2. The method as claimed in claim 1, wherein the cell-based composition is administered by way of intravenous infusion.

3. The method as claimed in claim 1, wherein the therapeutically effective amount is from 0.25 million to 3.0 million cells/kg body weight.

4. The method as claimed in claim 2, wherein the infusion is carried out in a period ranging from 30 minutes to 2 hours.

5. The method of claim 1, wherein the suspension of mesenchymal stem cells is derived from cryopreserved mesenchymal stem cells containing from 25 million to 35 million cells per cryovial.

6. The method as claimed in claim 5, wherein the cell-based composition is administered by way of intravenous infusion.

7. The method as claimed in claim 6, wherein the therapeutically effective amount is from 0.25 million to 3.0 million cells/kg body weight.

8. The method as claimed in claim 6, wherein the infusion is carried out in a period ranging from 30 minutes to 2 hours.

9. The method of claim 1, wherein the suspension of mesenchymal stem cells is derived from human umbilical cord, bone marrow, fat tissue, peripheral blood or tooth pulp.

10. The method as claimed in claim 9, wherein the cell-based composition is administered by way of intravenous infusion.

11. The method as claimed in claim 10, wherein the therapeutically effective amount is from 0.25 million to 3.0 million cells/kg body weight.

12. The method as claimed in claim 10, wherein the infusion is carried out in a period ranging from 30 minutes to 2 hours.

13. The method of claim 1, wherein the suspension of mesenchymal stem cells is positive for a selected group of surface markers including CD73, CD90, and CD105, and negative for a selected group of surface markers including CD34, CD45, and HLA-DR.

14. The method as claimed in claim 13, wherein the cell-based composition is administered by way of intravenous infusion.

15. The method as claimed in claim 14, wherein the therapeutically effective amount is from 0.25 million to 3.0 million cells/kg body weight.

16. The method as claimed in claim 14, wherein the infusion is carried out in a period ranging from 30 minutes to 2 hours.

* * * * *

UNITED STATES PATENT AND TRADEMARK OFFICE
CERTIFICATE OF CORRECTION

PATENT NO. : 10,278,993 B2
APPLICATION NO. : 15/597724
DATED : May 7, 2019
INVENTOR(S) : Bernard Sze-Piaw Chin et al.

It is certified that error appears in the above-identified patent and that said Letters Patent is hereby corrected as shown below:

In the Drawings

Replace FIGS. 4 and 5 with FIGS. 4 and 5 as shown on the attached page.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*